United States Patent
Fleischer

(10) Patent No.: US 9,266,973 B2
(45) Date of Patent: Feb. 23, 2016

(54) SYSTEMS AND METHODS FOR UTILIZING AND RECOVERING CHITOSAN TO PROCESS BIOLOGICAL MATERIAL

(71) Applicant: Daniel Fleischer, Oakland, CA (US)

(72) Inventor: Daniel Fleischer, Oakland, CA (US)

(73) Assignee: Aurora Algae, Inc., Hayward, CA (US)

( * ) Notice: Subject to any disclaimer, the term of this patent is extended or adjusted under 35 U.S.C. 154(b) by 0 days.

(21) Appl. No.: 13/839,647

(22) Filed: Mar. 15, 2013

(65) Prior Publication Data

US 2014/0273176 A1    Sep. 18, 2014

(51) Int. Cl.

| C08B 37/08 | (2006.01) |
|---|---|
| C12N 1/02 | (2006.01) |
| C08B 37/00 | (2006.01) |
| C12P 19/04 | (2006.01) |
| C12P 19/26 | (2006.01) |
| C12M 1/00 | (2006.01) |

(52) U.S. Cl.
CPC .......... *C08B 37/003* (2013.01); *C08B 37/0003* (2013.01); *C12M 47/02* (2013.01); *C12P 19/04* (2013.01); *C12P 19/26* (2013.01)

(58) Field of Classification Search
CPC ................................ C08B 37/003; C12N 1/02
USPC .................................. 435/261, 308.1; 536/20
See application file for complete search history.

(56) References Cited

U.S. PATENT DOCUMENTS

| 1,926,780 | A | 9/1933 | Lippincott |
|---|---|---|---|
| 2,730,190 | A | 1/1956 | Brown et al. |
| 2,766,203 | A | 10/1956 | Brown et al. |
| 3,175,687 | A | 3/1965 | Jones |
| 3,468,057 | A | 9/1969 | Buisson et al. |
| 3,642,844 | A | 2/1972 | Forbes |
| 3,897,000 | A | 7/1975 | Mandt |
| 3,962,466 | A | 6/1976 | Nakabayashi |
| 4,003,337 | A | 1/1977 | Moore |
| 4,065,875 | A | 1/1978 | Sma |
| 4,159,944 | A | 7/1979 | Erickson et al. |
| 4,253,271 | A | 3/1981 | Raymond |
| 4,267,038 | A | 5/1981 | Thompson |
| 4,341,038 | A | 7/1982 | Bloch et al. |
| 4,365,938 | A | 12/1982 | Warinner |
| 4,535,060 | A | 8/1985 | Comai |
| 4,658,757 | A | 4/1987 | Cook |
| 5,105,085 | A | 4/1992 | McGuire et al. |
| 5,130,242 | A | 7/1992 | Barclay |
| 5,180,499 | A | 1/1993 | Hinson et al. |
| 5,244,921 | A | 9/1993 | Kyle et al. |
| 5,275,732 | A | 1/1994 | Wang et al. |
| 5,338,673 | A | 8/1994 | Thepenier et al. |
| 5,382,358 | A * | 1/1995 | Yeh ............... 210/194 |
| 5,478,208 | A | 12/1995 | Kasai et al. |
| 5,527,456 | A | 6/1996 | Jensen |
| 5,539,133 | A | 7/1996 | Kohn et al. |
| 5,567,732 | A | 10/1996 | Kyle et al. |
| 5,656,667 | A | 8/1997 | Breivik et al. |
| 5,658,767 | A | 8/1997 | Kyle |
| 5,661,017 | A | 8/1997 | Dunahay et al. |
| 5,668,298 | A | 9/1997 | Waldron |
| 5,776,349 | A | 7/1998 | Guelcher et al. |
| 6,117,313 | A | 9/2000 | Goldman et al. |
| 6,143,562 | A | 11/2000 | Trulson et al. |
| 6,166,231 | A | 12/2000 | Hoeksema |
| 6,372,460 | B1 | 4/2002 | Gladue et al. |
| 6,524,486 | B2 | 2/2003 | Borodyanski et al. |
| 6,579,714 | B1 | 6/2003 | Hirabayashi et al. |
| 6,736,572 | B2 | 5/2004 | Geraghty |
| 6,750,048 | B2 | 6/2004 | Ruecker et al. |
| 6,768,015 | B1 | 7/2004 | Luxem et al. |
| 6,831,040 | B1 | 12/2004 | Unkefer et al. |
| 7,381,326 | B2 | 6/2008 | Haddas |
| 7,582,784 | B2 | 9/2009 | Banavali et al. |
| 7,767,837 | B2 | 8/2010 | Elliott |
| 7,868,195 | B2 | 1/2011 | Fleischer et al. |
| 7,883,882 | B2 | 2/2011 | Franklin et al. |
| 8,088,614 | B2 | 1/2012 | Vick et al. |
| 8,404,473 | B2 | 3/2013 | Kilian et al. |
| 8,569,530 | B2 | 10/2013 | Hippler et al. |

(Continued)

FOREIGN PATENT DOCUMENTS

| AU | 2010313246 | 5/2012 |
|---|---|---|
| JP | 09-024362 | 1/1997 |

(Continued)

OTHER PUBLICATIONS

Schlesinger et al., Inexpensive non-toxic flocculation of microalgae contradicts theories; overcoming a major hurdle to bulk algal production, Biotechnology Advances 30 (2012) 1023-1030.*
Wikipedia, Static Mixer, Accessed Dec. 7, 2014, Online at: en.wikipedia.org/wiki/ Static_mixer.*
International Search Report and Written Opinion of the International Searching Authority mailed Aug. 28, 2008 for Application No. PCT/US2007/023943, filed Nov. 13, 2007.
Santin-Montanya, et al. "Optimal Growth of Dunaliella Primolecta in Axenic Conditions to Assay Herbicides," Chemosphere, 66, Elsevier 2006, p. 1315-1322.
Felix, R. "Use of the cell wall-less alga Dunaliella bioculata in herbicide screening tests," Annals of Applied Biology, 113, 1988, pp. 55-60.
Janssen, M. et al. "Phytosynthetic efficiency of Dunaliella tertiolecta under short light/dark cycles," Enzyme and Microbial Technology, 29, 2001, p. 298-305.

(Continued)

*Primary Examiner* — Karen Cochrane Carlson
*Assistant Examiner* — Jennifer M. H. Tichy
(74) *Attorney, Agent, or Firm* — Carr & Ferrell LLP

(57) ABSTRACT

Systems and methods for processing biological material utilizing chitosan are provided herein. Methods may include the steps of reducing the pH of an amount of culture to about 5 to 7, incorporating an amount of a chitosan solution into the culture to form a mixture, wherein chitosan in the chitosan solution binds to the biological material; increasing the pH of the culture to about 7 to 10, to flocculate biological material in the culture, concentrating the flocculates, reducing the pH of the concentrated flocculates to about 3 to 5, and separating the recovered chitosan solution from the concentrated biological material.

14 Claims, 5 Drawing Sheets

(56) References Cited

U.S. PATENT DOCUMENTS

| | | | |
|---|---|---|---|
| 8,747,930 B2 | 6/2014 | Fleischer et al. | |
| 8,765,983 B2 | 7/2014 | Fleischer et al. | |
| 8,865,452 B2 | 10/2014 | Radaelli et al. | |
| 8,926,844 B2 | 1/2015 | Parsheh et al. | |
| 9,101,942 B2 | 8/2015 | Rice et al. | |
| 2003/0199490 A1 | 10/2003 | Antoni-Zimmermann et al. | |
| 2004/0121447 A1 | 6/2004 | Fournier | |
| 2004/0161364 A1 | 8/2004 | Carlson | |
| 2004/0262219 A1 | 12/2004 | Jensen | |
| 2005/0048474 A1 | 3/2005 | Amburgey, Jr. | |
| 2005/0064577 A1 | 3/2005 | Berzin | |
| 2005/0159593 A1* | 7/2005 | Struszczyk et al. | 536/124 |
| 2005/0164192 A1 | 7/2005 | Graham et al. | |
| 2005/0170479 A1 | 8/2005 | Weaver et al. | |
| 2005/0260553 A1 | 11/2005 | Berzin | |
| 2005/0273885 A1 | 12/2005 | Singh et al. | |
| 2006/0045750 A1 | 3/2006 | Stiles | |
| 2006/0101535 A1 | 5/2006 | Forster et al. | |
| 2006/0122410 A1 | 6/2006 | Fichtali et al. | |
| 2006/0166243 A1 | 7/2006 | Su et al. | |
| 2006/0277632 A1* | 12/2006 | Carr et al. | 800/284 |
| 2007/0102371 A1 | 5/2007 | Bhalchandra et al. | |
| 2008/0118964 A1 | 5/2008 | Huntley et al. | |
| 2008/0120749 A1 | 5/2008 | Melis et al. | |
| 2008/0155888 A1 | 7/2008 | Vick et al. | |
| 2008/0160591 A1 | 7/2008 | Willson et al. | |
| 2008/0160593 A1 | 7/2008 | Oyler | |
| 2008/0194029 A1 | 8/2008 | Hegemann et al. | |
| 2008/0268302 A1 | 10/2008 | McCall | |
| 2008/0275260 A1 | 11/2008 | Elliott | |
| 2008/0293132 A1 | 11/2008 | Goldman et al. | |
| 2009/0011492 A1 | 1/2009 | Berzin | |
| 2009/0029445 A1 | 1/2009 | Eckelberry et al. | |
| 2009/0081748 A1 | 3/2009 | Oyler | |
| 2009/0148931 A1 | 6/2009 | Wilkerson et al. | |
| 2009/0151241 A1 | 6/2009 | Dressler et al. | |
| 2009/0162919 A1 | 6/2009 | Radaelli et al. | |
| 2009/0234146 A1 | 9/2009 | Cooney et al. | |
| 2009/0317857 A1 | 12/2009 | Vick et al. | |
| 2009/0317878 A1 | 12/2009 | Champagne et al. | |
| 2009/0317904 A1 | 12/2009 | Vick et al. | |
| 2009/0325270 A1 | 12/2009 | Vick et al. | |
| 2010/0022393 A1 | 1/2010 | Vick | |
| 2010/0068772 A1 | 3/2010 | Downey | |
| 2010/0151540 A1 | 6/2010 | Gordon et al. | |
| 2010/0183744 A1 | 7/2010 | Weissman et al. | |
| 2010/0196995 A1 | 8/2010 | Weissman et al. | |
| 2010/0210003 A1 | 8/2010 | King et al. | |
| 2010/0210832 A1 | 8/2010 | Kilian et al. | |
| 2010/0260618 A1 | 10/2010 | Parsheh et al. | |
| 2010/0261922 A1 | 10/2010 | Fleischer et al. | |
| 2010/0314324 A1 | 12/2010 | Rice et al. | |
| 2010/0317088 A1 | 12/2010 | Radaelli et al. | |
| 2010/0327077 A1 | 12/2010 | Parsheh et al. | |
| 2010/0330643 A1 | 12/2010 | Kilian et al. | |
| 2010/0330658 A1 | 12/2010 | Fleischer et al. | |
| 2011/0041386 A1 | 2/2011 | Fleischer et al. | |
| 2011/0070639 A1 | 3/2011 | Pandit et al. | |
| 2011/0072713 A1 | 3/2011 | Fleischer et al. | |
| 2011/0136212 A1 | 6/2011 | Parsheh et al. | |
| 2011/0196163 A1 | 8/2011 | Fleischer et al. | |
| 2011/0197306 A1 | 8/2011 | Bailey et al. | |
| 2011/0300568 A1 | 12/2011 | Parsheh et al. | |
| 2011/0313181 A1 | 12/2011 | Thompson et al. | |
| 2012/0129244 A1 | 5/2012 | Green et al. | |
| 2012/0225941 A1 | 9/2012 | Green | |
| 2013/0274490 A1 | 10/2013 | Hippler et al. | |
| 2014/0275613 A1 | 9/2014 | Hippler et al. | |

FOREIGN PATENT DOCUMENTS

| | | |
|---|---|---|
| JP | 2004300218 | 10/2004 |
| JP | 2008280252 | 11/2008 |
| WO | WO2004106238 | 12/2004 |
| WO | WO2008060571 | 5/2008 |
| WO | WO2009037683 | 3/2009 |
| WO | WO2009082696 | 7/2009 |
| WO | WO2011053867 | 5/2011 |
| WO | WO2014151116 | 9/2014 |

OTHER PUBLICATIONS

Saenz, M.E., "Effects of Technical Grade and a Commercial Formulation of Glyphosate on Algal Population Growth," Bulletin of Environmental Contamination Toxicology, 1997, 59: pates 638-644.

Endo et al. "Inactivation of Blasticidin S by Bacillus Cereus II. Isolation and Characterization of a Plasmid, pBSR 8, from Bacillus Cereus," The Journal of Antibiotics 41 (2): 271-2589-2601. Feb. 1988.

Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999).

Kindle et al., "Stable Nuclear Transformation of Chlamydomonas Using the Chlamydomonas Gene for Nitrate Reductase" The Journal of Cell Biology 109 (6, part 1) 1989: 2589-2601.

Prein et al. "A Novel Strategy for Constructing N-Terminal Chromosomal Fusions to Green Fluorescent Protein in the Yeast Saccharomyces cerevisiae" FEBS Letters 485 (2000) 29-34.

Schiedlmeier et al., "Nuclear Transformation of Volvox Carteri" Proceedings of the National Academy of Sciences USA 91(11): 5080-5084 (May 1994).

Wendland et al. "PCR-Based Methods Facilitate Targeted Gene Manipulations and Cloning Procedures" Curr.Gen. (2003) 44:115-123.

Molnar et al., "Highly Specific Gene Silencing by Artificial MicroRNAs in the Unicellular Agla Chlamydomonas reinhardtii," Plant Jour. ePub Jan. 17, 2009, vol. 58, No. 1, pp. 157-164 (Abstract Only).

Chen et al., "Conditional Production of a Functional Fish Growth Hormone in the Transgenic Line of Nannochloropsis oculata (Eustigmatophyceae)," J. Phycol. Jun. 2008, vol. 44, No. 3, pp. 768-776.

Nelson et al., "Targeted Disruption of NIT8 Gene in Chlamydomonas reinhardtii." Mol. Cell. Bio. Oct. 1995, vol. 15, No. 10, pp. 5762-5769.

Grima et al. "Recovery of Microalgal Biomass in Metabolites: Process Options and Economics," Biotechnology Advances 20, 2003, pp. 491-515.

Knuckey et al. "Production of Microalgal Concentrates by Flocculation and their Assessment as Aquaculture Feeds," Aquacultural Engineering 35, 2006, pp. 300-313.

Kureshy et al., "Effect of Ozone Treatment on Cultures of Nannochloropsis oculata, Isochrysis galbana, and Chaetoceros gracilis," Journal of the World Aquaculture Society, 1999, 30(4), pp. 473-480.

Csogor et al., "Light Distribution in a Novel Photobioreactor—Modelling for Optimization," Journal of Applied Phycology, vol. 13, 2001, pp. 325-333.

Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.

Zittelli et al., "Mass Cultivation of Nannochloropsis Sp. In Annular Reactors," Journal of Applied Phycology, vol. 15, pp. 107-113, Mar. 2003.

Strzepek et al., "Photosynthetic Architecture Differs in Coastal and Oceanic Diatoms," Nature, vol. 431, pp. 689-692, Oct. 2004.

Lee et al., "Isolation and Characterization of a Xanthophyll Aberrant Mutant of the Green Alga Nannochloropsis oculata," Marine Biotechnology, 2006, vol. 8, pp. 238-245.

NCBI entry EE109892 (Jul. 2006) [Retrieved from the Internet on Oct. 19, 2009, <http://www.ncbi.nlm.nih.gov/nucest/EE109892?ordinalops=1&itoo1=EntrezSystem2.Pentrez.Sequence.Sequence_ResultsPanel.Sequence_RVDocSum>].

Berberoglu et al., "Radiation Characteristics of Chlamydomonas reinhardtii CC125 and its truncated chlorophyll antenna transformants tla1, tlaX, and tla1-Cw+,"International Journal of Hydrogen Energy, 2008, vol. 33, pp. 6467-6483.

(56) References Cited

OTHER PUBLICATIONS

Ghirardi et al., "Photochemical Apparatus Organization in the Thylakoid Membrane of Hordeum vulgare wild type and chlorophyll b-less chlorina f2 mutant," Biochimica et Biophysica Act (BBA)—Bioengergetics, vol. 851, Issue 3, Oct. 1986, pp. 331-339 (abstract only).
Steinitz et al., "A mutant of the cyanobacterium Plectonema boryanum resistant to photooxidation," Plant Science Letters, vol. 16, Issues 2-3, 1979, pp. 327-335 (abstract only).
Koller et al., "Light Intensity During Leaf Growth Affects Chlorophyll Concentration and CO2 Assimilation of a Soybean Chlorophyll Mutant," Crop Science, 1974, vol. 14, pp. 779-782 (abstract only).
Shikanai et al., "Identification and Characterization of Arabidopsis Mutants with Reduced Quenching of Chlorophyll Fluorescence," Plant and Cell Physiology, 1999, vol. 40, No. 11, pp. 1134-1142 (abstract only).
Hedenskog, G. et al., "Investigation of Some Methods for Increasing the Digestibility in Vitro of Microalgae," Biotechnology and Bioengineering, vol. XI, pp. 37-51, 1969.
Loury, "Method for Rapid Conversion of Fats to Methyl Esters," Revue Francaise des Corps Gras, 1967, 14(6), 383-389 (abstract only).
Cravotto et al., "Improved Extraction of Vegetable Oils under high-intensity Ultrasound and/or Microwaves," Ultrasonics Sonochemistry, 15: 898-902, 2008.
Ben-Amotz, Ami. "Large-Scale Open Algae Ponds," presented at the NREL-AFOSR Joint Workshop on Algal Oil for Get Fuel Production in Feb. 2008.
Ebeling et al., "Design and Operation of a Zero-Exchange Mixed-Cell Raceway Production System," 2nd Int'l Sustainable Marine Fish Culture Conference and Workshop, Oct. 2005.
Ebeling et al., "Mixed-Cell Raceway: Engineering Design Criteria, Construction, and Hydraulic Characterization," North American Journal of Aquaculture, 2005, 67: 193-201 (abstract only).
Labatut et al., "Hydrodynamics of a Large-Scale Mixed-Cell Raceway (MCR): Experimental Studies," Aquacultural Engineering vol. 37, Issue 2, Sep. 2007, pp. 132-143.
Kizilisoley et al., "Micro-Algae Growth Technology Systems," Presented by Selim Helacioglu, Soley Institute, 2008.
Dunstan et al., "Changes in the Lipid Composition and Maximisation of the Polyunsaturated Fatty Acid Content of Three Microalgae Grown in Mass Culture," Journal of Applied Phycology, 5, pp. 71-83, 1993.
Carvalheiro et al., "Hemicellulose Biorefineries: A Review on Biomass Pretreatments," Journal of Scientific & Industrial Research, vol. 67, Nov. 2008, pp. 849-864.
Lotero et al., "Synthesis of Biodiesel via Acid Catalysis," Ind. Eng. Chem. Res., 2005, pp. 5353-5363.
Gouveia et al., "Microalgae as a raw material for biofuels production," J. Ind. Microbiol. Biotechnol, 2009, vol. 36, 269-274.
International Search Report and Written Opinion of the International Searching Authority mailed Jan. 6, 2011 for Application No. PCT/US2010/054861, filed Oct. 29, 2010.
Chen et al., "Subcritical co-solvents extraction of lipid from wet microalgae pastes of Nannochloropsis sp.," Eur. J. Lipid Sci. Technol., vol. 114, 2012, pp. 205-212.
Wang et al., "Lipid and Biomass Distribution and Recovery from Two Microalgae by Aqueous and Alcohol Processing," Journal of the American Oil Chemists' Society, vol. 38, Issue 2, Jul. 2011, pp. 335-345.
Pitipanapong et al., "New approach for extraction of charantin from Momordica charantia with pressurized liquid extraction," Separation and Purification Technology, vol. 52, Issue 3, Jan. 2007.
International Search Report and Written Opinion of the International Searching Authority mailed Feb. 5, 2009 for Application No. PCT/US2008/087722, filed Dec. 19, 2008.
Examination Report mailed Aug. 15, 2013 in Australian Application No. 2010313246 filed Oct. 29, 2010.
Second Examination Report mailed Dec. 17, 2013 in Australian Application No. 2010313246 filed Oct. 29, 2010.
Lubian, L. M., "Concentrating Cultured Marine Microalgae with Chitosan." Aquaculture Engineering, 8, 257-265 (1989).
Divakaran, R. & Sivasankara Pillai, VN, "Flocculation of Algae Using Chitosan." Journal of Applied Phycology, 14, 419-422 (2002).
Farid, M. S., Shariati, A., Badakhshan, A., & Anvaripour, B., "Using Nano-Chitosan for Harvesting Microalga Nannochloropsis sp." Bioresource Technology, 131, 555-559 (2013).
Notice of Allowance mailed Jul. 23, 2014 in Australian Application No. 2010313246 filed Oct. 29, 2010.
International Search Report and Written Opinion of the International Searching Authority mailed Jul. 7, 2014 for Application No. PCT/US2014/025019, filed Mar. 12, 2014.

* cited by examiner

SYSTEMS AND METHODS FOR UTILIZING AND RECOVERING CHITOSAN TO PROCESS BIOLOGICAL MATERIAL

FIELD OF INVENTION

The present invention relates generally to systems and methods that process biological material, and more particularly, but not by way of limitation, to systems and methods that utilize and recover chitosan for processing biological material.

SUMMARY OF THE INVENTION

Provided herein are exemplary systems and methods for processing biological material. Exemplary methods may include at least the steps of: (a) reducing the pH of an amount of culture to about 5 to 7, inclusive, the amount of culture including an amount of biological material suspended within a fluid; (b) incorporating an amount of a chitosan solution into the culture to form a mixture, wherein chitosan in the chitosan solution binds to the biological material; (c) increasing the pH of the mixture to about 7 to 10, inclusive, to cause the biological material bound to the chitosan to form flocculates that are dispersed in the fluid; (d) concentrating the flocculates by separating the flocculates from the fluid; (e) reducing the pH of the concentrated flocculates to about 3 to 5, inclusive, to disassociate the chitosan from the concentrated flocculates, causing the chitosan to combine with the fluid to create a recovered chitosan solution; and (f) separating the recovered chitosan solution from the concentrated biological material.

Additional exemplary embodiments include methods for utilizing and recovering chitosan to process biological material that include the steps of: (a) reducing the pH of an amount of culture to about 5 to 7, inclusive, the amount of culture including an amount of biological material suspended within a fluid; (b) incorporating an amount of a chitosan solution into the culture to form a mixture, wherein chitosan in the chitosan solution binds to the biological material; (c) increasing the pH of the mixture to about 7 to 10, inclusive, to cause the biological material bound to the chitosan to form flocculates that are dispersed in the fluid; (d) concentrating the flocculates by separating the flocculates dispersed in the fluid; (e) reducing the pH of the concentrated flocculates to about 3 to 5, inclusive, to disassociate the chitosan from the concentrated flocculates causing the chitosan to combine with the fluid to create a recovered chitosan solution; (f) separating the recovered chitosan solution from the concentrated biological material; (g) removing additional chitosan from concentrated biological material by: (1) resuspending the concentrated biological material in fresh water; and (2) mechanically processing the resuspended concentration of biological material in such a way that the additional chitosan separates from the concentrated biological material into the fresh water to form a second recovered chitosan solution; and (3) combining the additional chitosan in the fresh water with the recovered chitosan solution.

In other embodiments, systems adapted to utilize and recover chitosan for processing biological material may include (a) a culture source that retains culture, the culture including an amount of biological material suspended within a fluid; (b) a mixer in fluid communication with the culture source and the acid source, the mixer adapted to reduce the pH of the amount of culture to about 5 to 7, inclusive, by facilitating one or more chemical processes within the culture; (c) a flocculation apparatus receiving the culture and incorporating an amount of a chitosan solution into the culture to form a mixture, wherein chitosan in the chitosan solution binds to the biological material, the flocculation apparatus adapted to receive an amount of a base from a base source to increase the pH of the mixture to about 7 to 10, inclusive, to cause the biological material bound to the chitosan to form flocculates that are dispersed in the fluid; (d) a separator apparatus to separate the flocculates from the fluid to concentrate the flocculates, the separator apparatus being adapted to receive an amount of an acid to reduce the pH of the concentrated flocculates to about 3 to 5, inclusive, to remove additional chitosan from the concentrated flocculates; (e) wherein the additional chitosan and the concentrated biological material are mechanically processed by separator apparatus to separate the additional chitosan from the concentrated biological material to produce additional recovered chitosan solution; and (f) wherein the additional recovered chitosan solution is incorporated with the recovered chitosan solution.

According to some embodiments, methods for efficiently producing biological materials for utilization in the production of biofuels, protein, nutritional oils and other bioproducts may include (a) reducing the pH of an amount of culture to about 5 to 7, inclusive, the amount of culture including an amount of biological material suspended within a fluid; (b) incorporating an amount of a chitosan solution into the culture to form a mixture, wherein chitosan in the chitosan solution binds to the biological material; (c) increasing the pH of the mixture to about 7 to 10, inclusive, to cause the biological material bound to the chitosan to form flocculates that are dispersed in the fluid; (d) concentrating the flocculates by separating the flocculates from the fluid; (e) reducing the pH of the concentrated flocculates to about 3 to 5, inclusive, to disassociate the chitosan from the concentrated flocculates causing the chitosan to combine with the fluid to create a recovered chitosan solution; (f) separating the recovered chitosan solution from the concentrated biological material; and (g) processing the concentrated biological material in such a way that a biofuel, protein, nutritional oil or other bioproduct is produced.

BRIEF DESCRIPTION OF THE DRAWINGS

Certain embodiments of the present invention are illustrated by the accompanying figures. It will be understood that the figures are not necessarily to scale and that details (e.g., dimensions) not necessary for an understanding of the invention or that render other details difficult to perceive may be omitted. It will be understood that the invention is not necessarily limited to the particular embodiments illustrated herein.

DETAILED DESCRIPTION

Figure 1:
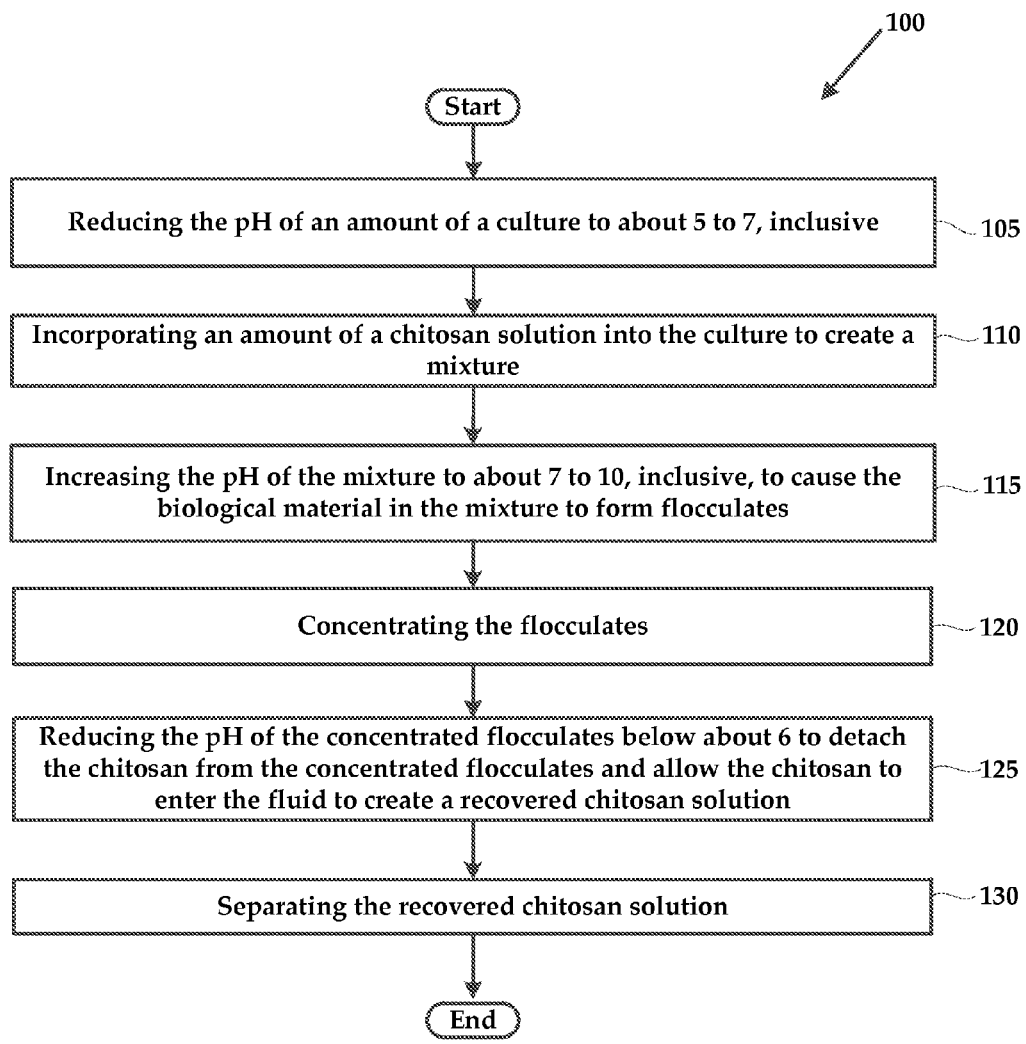
FIG. 1 illustrates a flow diagram of a method for utilizing and recovering chitosan to process biological material.

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings with like reference characters.

Generally speaking, challenges in developing economically sustainable, large-scale production of microalgae products include issues relative to the separation of the cultivated algae from the aqueous growth media. When using open pond cultivation strategies, microalgae are generally harvested when the culture includes between 100 and 400 milligrams per liter, ash-free dry weight of microalgae biomass. Thus, it is inferred that about 99.99 to 99.96 percent of the culture is an aqueous fluid.

It will be understood that for purposes of brevity, the systems and methods described herein will be directed towards the processing of microalgae, although one of ordinary skill in the art will appreciate that the systems and methods described herein may be utilized to process many other types of biological materials (e.g., organic materials) that are suspended in a fluid.

One non-limiting example of a biological material suspended in a fluid includes microalgae of the genus *Nannochloropsis* that has been incorporated into a cultivation fluid such as seawater. The combination of the microalgae within the cultivation fluid may be referred to as the "culture." The culture fluid may be placed into a raceway reactor or a photobioreactor to allow the microalgae to mature. Upon maturation, the microalgae are harvested by way of one or more separation techniques that separate the microalgae from the cultivation fluid.

Common microalgae separation techniques include filtration, decanting and centrifugation, with centrifugation being a very effective process. Unfortunately, centrifugation may not be economically feasible due to the high power consumption and capital costs required to operate centrifuges that are of sufficient size to engender such concentration factors. Filtration through a screen or membrane works well for large and or colonial microalgae, however it is not capital efficient for unicellular species with small cell diameter, such as microalgae from the genus *Nannochloropsis*, due to the large membrane area required to achieve sufficient transmembrane flux at the necessary retentate concentration.

Other methods of separating microalgae such as flocculation, flotation with dissolved air, frothing, settling and decanting, or flocculation enhanced filtration, remain the most promising techniques for harvesting microalgae from dilute cultures (e.g., a biological material suspended in a fluid).

An additional method for harvesting algae includes autoflocculation. Autoflocculation may entail raising the pH of the culture by reducing the amount of carbon dioxide that is input into the culture while the culture is being exposed to full sunlight. However, autoflocculation requires reducing the amount of $CO_2$ input at the peak levels of productivity and hence may reduce total biomass yield.

Numerous flocculation agents exist which may cause flocculation of the microalgae, enabling the microalgae to clump together into flakes or "flocculates." These flocculates may then need to be floated, settled, or filtered by the methods described above. Flocculation agents that are based on iron, aluminum, zinc, and similar metal ions are very effective for flocculating small microalgae, even in marine systems. However, the use of such flocculation agents for harvesting microalgae results in the presence of unwanted metals in the resulting microalgae biomass. The presence of such metals reduces the value of the microalgae biomass as a protein rich food. Removal of the metal residue from the microalgae biomass requires reducing the pH of the microalgae biomass to a very low level, which may be difficult to achieve in the context of large-scale extractions and may produce unwanted side-reactions in the microalgae biomass.

In addition, some flocculation methods utilize organic polymer flocculation agents such as polyacrylamides. Unfortunately, the acrylamide monomers of polyacrylamides may be carcinogenic when consumed by animals. Therefore, organic polymer flocculation agents may not be utilized to harvest microalgae for processes that incorporate microalgae in products intended as an animal feedstock.

Additionally, methods that utilize flocculation for harvesting microalgae by raising the pH of the culture above 9.7 with calcium hydroxide or sodium hydroxide may result in unwieldy carbonate or hydroxide deposits in the final product and in the harvesting equipment, which may decrease the value of the microalgae biomass and increase equipment maintenance costs.

Therefore, the systems and methods provided herein may utilize chitosan as a flocculation agent to harvest microalgae. As background, chitosan is the polyglucosamine product of the deacetylation of chitin, which is an abundant biopolymer found in the exoskeletons of crustaceans, shellfish (shrimp, crabs, lobsters), insects, in the cell walls of fungi and some algae, as well as in molluscan raduli and cephalopod beaks.

Most chitosan solutions utilized for various chemical processes may be produced by methods that include numerous steps such as deproteinizing chitinous biomass, demineralizing, drying, deacetylation, dissolving, and drying. It will be understood that in some cases, it may be possible to only deacetylate the chitinous biomass and then dissolve the resulting crude chitosan into a crude chitosan solution. This crude chitosan solution may be used for harvesting microalgae via flocculation. It is noteworthy that crude chitosan may be much less expensive to produce and functions well as a flocculation agent. Moreover, crude chitosan may be produced from waste chitinous biomass, such as spent fermentation fungi, insect corpses, shrimp-shells, and the like.

Because chitosan contains a free amine functional group, which can become protonated, chitosan can function as a cationic polymer. This positive charge enables the chitosan polymer to form ionic bonds with the negatively charged cell surface of most biological materials such as microalgae, thus bridging cellular microalgae together and engendering flocculation.

Moreover, chitosan is edible, nontoxic, is generally recognized as safe, and has been approved for use in human food products. However, chitosan is much more expensive than other flocculation agents such as metals or polyacrylamides. Thus to be an economically sustainable flocculation agent, the chitosan must be recovered and reused. Therefore, the systems and methods provided herein may be adapted to utilize chitosan as a flocculation agent and recover the chitosan for further use, thus enabling cost effective harvesting of biological materials such as microalgae for use in food products and animal feeds.

Referring now to FIG. 1, a method 100 for processing biological materials such as microalgae is shown. The method 100 includes the step 105 of reducing the pH of an amount of a culture to about 5 to 7, inclusive. The amount of the culture may include an amount of biological material (e.g., microalgae) suspended within a fluid (e.g., a cultivation fluid having water as a major component). It is noteworthy that unless the meaning is clearly to the contrary, all ranges set forth herein are deemed to be inclusive of endpoints.

It will be understood that methods for reducing the pH of an amount of the culture may include sparging an amount of carbon dioxide into the culture. In other embodiments, the pH of the culture may be reduced by combining the culture with an amount of an acid such as hydrochloric acid, although one of ordinary skill in the art will appreciate that many other types of acids may likewise be utilized in accordance with the present disclosure.

After the pH of the culture has been reduced, the method 100 may include the step 110 of incorporating an amount of a chitosan solution into the culture. The amount of the chitosan solution incorporated into the culture may include about 0.5 to 200 milligrams of chitosan solution per liter of culture. The chitosan solution may be combined with the culture to create a mixture.

It will be understood that chitosan may be more soluble in seawater having a pH of about 6, with solubility decreasing as pH increases. Moreover, even though chitosan binds to the microalgae when mixed with the culture, because the pH of the culture has been reduced in the first step 105, very little, if any, flocculation occurs. As such, the method 100 may include the step 115 of increasing the pH of the mixture to about 7 to 10, inclusive, to cause the biological material bound to the chitosan to form flocculates. These flocculates separate from the fluid and are dispersed throughout.

Stated otherwise, when the pH of the mixture is raised, the microalgae flocculate as the chitosan to which they are bound becomes insoluble. It will be understood that if the chitosan is added to a culture already of elevated pH 8.5, for example (e.g., the pH of the culture before the first step 105), then flocculation may not occur even if the pH is raised further. In such cases, the chitosan may never bind with the microalgae and create flocculates.

On the other hand, if the culture is being grown at a pH of 8.5 and the pH of the mixture is reduced to about 6, the chitosan may then bind to the microalgae and create flocculates. As stated previously, the positive charge of the chitosan enables the chitosan polymer to form ionic bonds with the negatively charged cell surface of microalgae, thus bridging microalgae together and engendering flocculation.

According to some embodiments, the pH of the mixture may be increased by combining the mixture with an amount of a base that includes at least one of calcium oxide, calcium hydroxide, sodium hydroxide, magnesium hydroxide, ammonium hydroxide, and combinations thereof.

In some embodiments, the amount of the base combined with the mixture may include a sufficient amount to raise the pH of the mixture a sufficient amount to cause substantially all of the suspended biological material to form flocculates.

After the creation of flocculates, the method 100 may include the step 120 of concentrating the flocculates by separating the flocculates from the fluid. According to some embodiments concentrating may include dissolved air flotation, centrifugation, decanting, filtering, or other suitable mechanical or chemical methods for separating the flocculates from the fluid that would be known to one of ordinary skill in the art with the present disclosure before them.

It will be understood that a small amount of residual fluid may be left with the concentrated flocculates to facilitate the next step 125 of the method 100. Step 125 includes reducing the pH of the concentrated flocculates mixture (e.g., concentrated flocculates plus the residual fluid) below about 5 to detach the chitosan from the flocculates and return the chitosan to a soluble form. Therefore, the chitosan may disperse back into the residual fluid to produce a recovered chitosan solution.

The method 100 may then include the step 130 of separating the recovered chitosan solution from the now deflocculated biological material by mechanical processes such as filtration, decanting, or centrifugation.

According to some exemplary methods, the biological material and recovered chitosan solution may be centrifuged to separate a supernatant (centrate) that contains the dissolved chitosan (e.g., recovered chitosan solution), which may be reused as a flocculation agent in this form from a centrifugate.

The centrifugate includes the dewatered microalgae paste. In some embodiments, the centrifugate may be resuspended in fresh water and centrifuged again. The centrate (e.g., additional chitosan solution) produced by this second centrifugation may include an additional amount of entrained soluble chitosan, provided that the resuspension mixture is maintained at a pH sufficiently low to maintain chitosan solubility, which may be combined with the recovered chitosan solution and reused as flocculation agent in subsequent executions of the method 100.

It will be understood that the additional step of resuspending and recentrifuging the concentrated flocculates may produce a dewatered microalgae paste that includes a substantially reduced amount of ash content relative to dewatered microalgae paste that has not been resuspended and recentrifuged, thereby raising its value as a food.

Figure 2A:
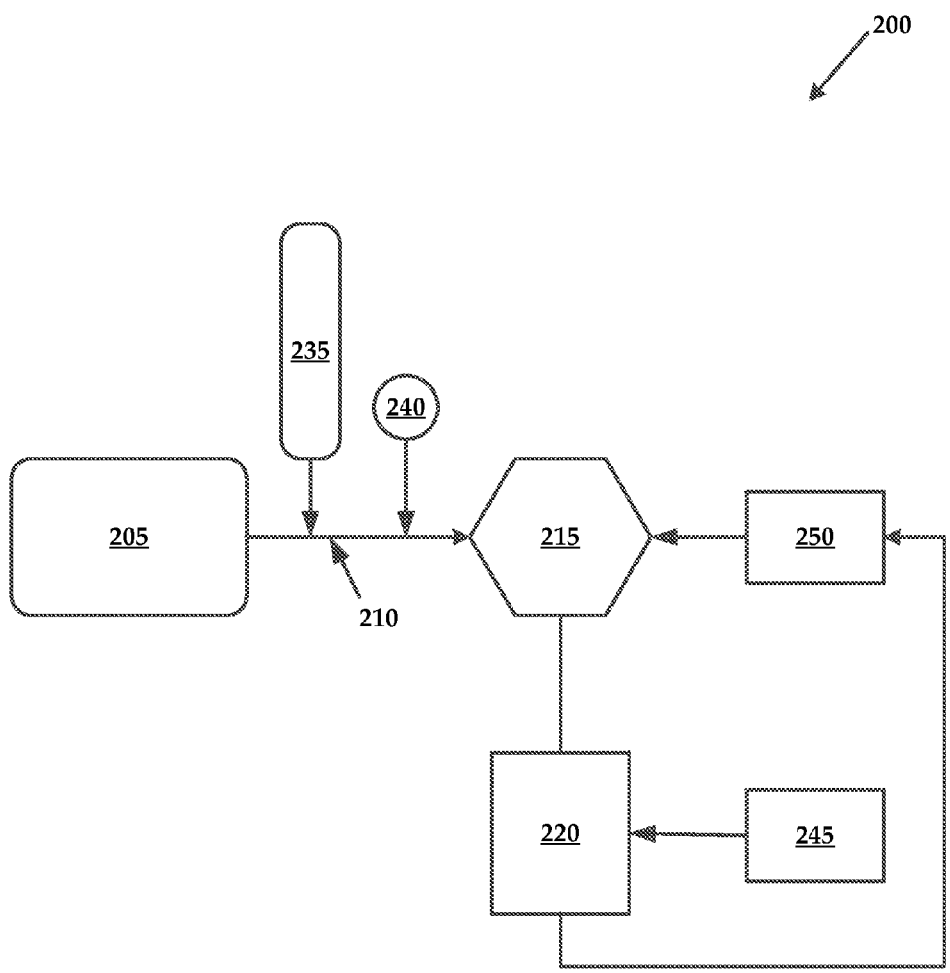
FIG. 2A illustrates a schematic diagram of a system adapted to utilize and recover chitosan for processing biological material.

Referring now to FIG. 2A, an exemplary system 200 adapted to utilize and recover chitosan for processing biological material is shown. It will be understood that the system 200 may be utilized in batch processes. According to some embodiments, the system 200 may be generally described as including a culture source 205, a mixer 210, a flocculation apparatus 215, and a separator apparatus 220. While the system 200 has been disclosed as including the aforementioned components, one of ordinary skill in the art will appreciate that one or more additional components including devices, apparatuses, assemblies, or sub-assemblies may also be included in the system 200. Additionally, one or more of the components of system 200 may be combined together. For example, the mixer 210 and the flocculation apparatus 215 may be combined together.

In some embodiments, the culture source 205 may include any one of a number of apparatuses that are adapted to retain a culture such as microalgae dispersed in a cultivation fluid. Non-limiting examples of culture source 205 may include a raceway reactor or a photobioreactor.

The culture source 205 may be operatively connected to the flocculation apparatus 215 via the mixer 210, which may be implemented in the context of a conduit extending between the culture source 205 and the flocculation apparatus 215. The conduit facilitates fluid communication of the culture from the culture source 205 to the flocculation apparatus 215. In some embodiments, the conduit may include any one of a number of tubular devices such as a pipe.

In some embodiments, the mixer 210 may include one or more static mixers, although other types of mixers that would be known to one of ordinary skill in the art with the present disclosure before them are likewise contemplated for use in accordance with the present invention.

The system 200 may be adapted to reduce the pH of the amount of culture that is communicating through the conduit to about 5 to 7, inclusive, by facilitating one or more chemical processes. In some embodiments, the system 200 may include a sparger 235 associated with the conduit that injects an amount of carbon dioxide into the culture. The carbon dioxide combines with the culture and lowers the pH of the culture.

Although not shown, in some alternate embodiments, the system 200 may be adapted to introduce an amount of an acid (e.g., hydrochloric acid) into the conduit from an acid source. As the culture communicates through the conduit, the mixer 210 thoroughly incorporates the acid into the culture. To ensure that the culture is at an acceptable pH level, the system 200 may include a pH probe 240 adapted to measure the pH of the culture. The pH probe 240 may be positioned proximate the flocculation apparatus 215 to ensure that the pH of the culture is about 5 to 7, inclusive.

The culture may then enter the flocculation apparatus 215 where an amount of chitosan solution is introduced into the flocculation apparatus 215 via a chitosan solution source 250. The flocculation apparatus 215 may be adapted to fully combine the culture with the amount of the chitosan solution to create a mixture. When mixed, the chitosan in the chitosan solution forms ionic bonds with the microalgae cells in the mixture.

The flocculation apparatus 215 may be adapted to receive an amount of a base from a base source (not shown) to increase the pH of the mixture to about 7 to 10, inclusive, to cause microalgae that are bound to the chitosan to form flocculates that are dispersed in the fluid. As stated previously, when the pH of the mixture is increased, the microalgae flocculate together as the chitosan becomes insoluble.

Although not shown, in some embodiments, the flocculation apparatus 215 may include a container (not shown) that includes a dissolved air flotation system (also not shown). Bubbles created via the dissolved air flotation system percolate through the mixture, associate with the flocculates, and separate the flocculates from the fluid by carrying the flocculates to the surface of the fluid. Moreover, if the flocculation apparatus 215 includes a dissolved air flotation system, the flocculation apparatus 215 may also include a decanter adapted to remove the flocculates from the surface of the fluid to concentrate the flocculates.

In other embodiments, the flocculates and fluid may be communicated to the separator apparatus 220. In some embodiments, the separator apparatus 220 may include one or more filters or a centrifuge. If the separator apparatus 220 includes a centrifuge, the centrifuge may mechanically separate the flocculates from the fluid via centrifugation to concentrate the flocculates.

After the flocculates have been concentrated, the centrifuge may be adapted to receive an amount of an acid from an acid source 245 and combine the acid with the concentrated flocculates (along with residual fluid) to reduce the pH of the concentrated flocculates to about 3 to 5, inclusive, to remove chitosan bound to the concentrated flocculates. By reducing the pH of the concentrated flocculates, the chitosan may convert back to a soluble form and disperse into the residual fluid to create a recovered chitosan solution. Once the centrifuge has processed the recovered chitosan solution, the recovered chitosan solution may be communicated to the chitosan solution source 250 to be reutilized as a flocculating agent in the system 200.

It will be understood that the system 200 described above may be operated in either batch or continuous flow modes. With respect to batch modes, the system 200 may be adapted to receive batch amounts of the products from each of the various components of the system 200 to produce batches of processed microalgae. In contrast, continuous flow systems, described in greater detail with regard to system 265 (see FIG. 2C), constantly produce a predetermine amount of processed microalgae. Either batch or continuous flow methods produce processed microalgae that may be processed by one or more downstream systems and/or methods to extract biological oils, proteins and or products of value from the processed microalgae. The biological oils, proteins and or products of value may then be converted into biofuels, foods, pharmaceuticals or other products of added value. Therefore, the systems and methods disclosed herein provide mechanisms that increase the efficacy of biofuels and or the production of proteins, nutrients and pharmaceuticals.

The separator apparatus 220 (e.g., centrifuge) may also be adapted to receive an amount of fresh water in which the concentrated flocculates may be resuspended. The centrifuge may then mechanically process the resuspended flocculates such that the centrate produced by this second centrifugation includes an additional amount of entrained soluble chitosan. The additional amount of chitosan may be communicated to the chitosan solution source 250.

Figure 2B:
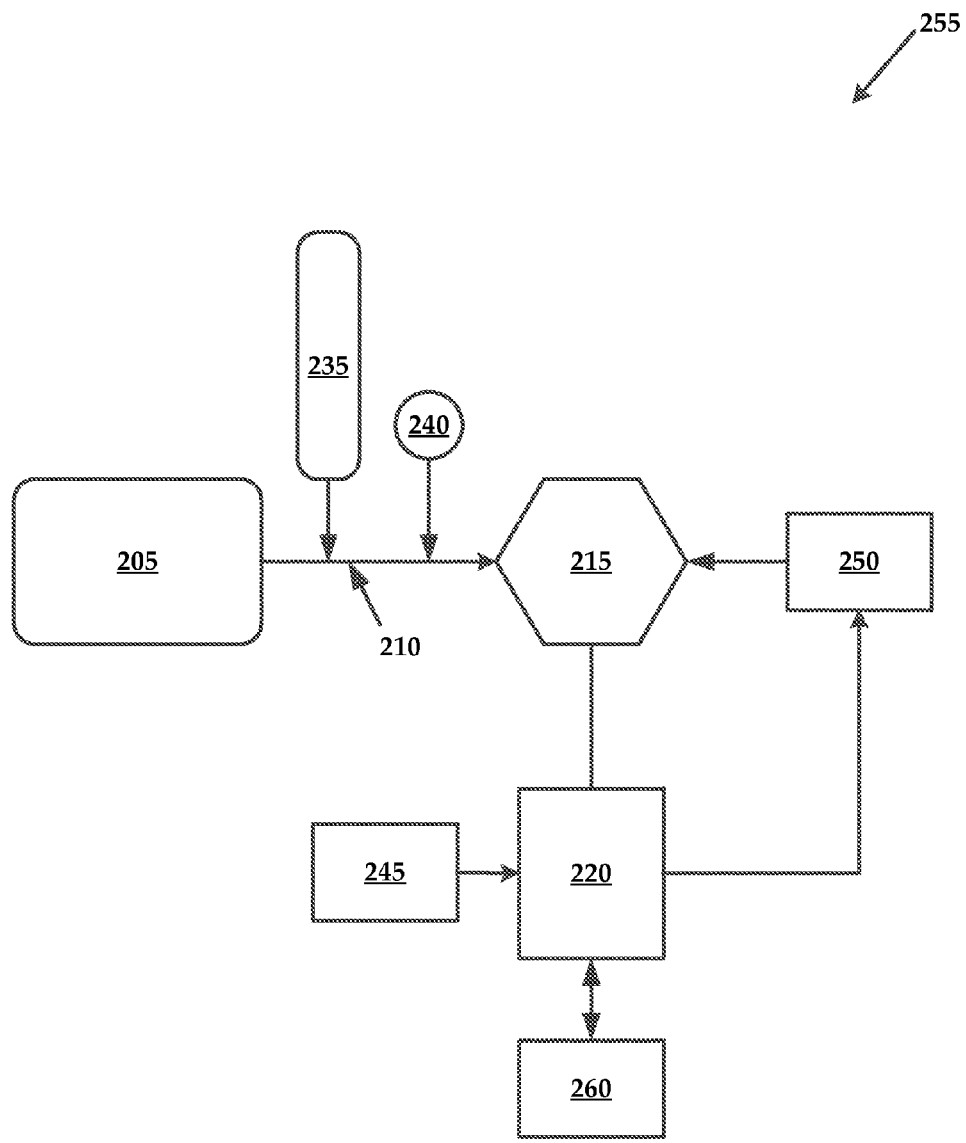
FIG. 2B illustrates a schematic diagram of an additional system adapted to utilize and recover chitosan for processing biological material.

Referring now to FIG. 2B, an additional embodiment of a system 255 adapted to utilize and recover chitosan for processing biological material is shown. It will be understood that the system 255 may include each of the components of system 200 (FIG. 2A) with the addition of a vessel 260.

More specifically, if the centrifuge (e.g., the separator apparatus 220) is unable to combine the concentrated flocculates with the acid, the concentrated flocculates may be communicated to a vessel 260. The vessel 260 may be adapted to mix the acid received from the acid source 245 with the concentrated flocculates. The mixture of concentrated biological material and acid may then be introduced into the centrifuge for further processing. The centrifuge may then separate the concentrated biological material from the recovered chitosan solution by centrifugation. Therefore, the supernatant (centrate) contains the recovered chitosan solution, which may be reused as a flocculating agent.

The vessel 260 may be adapted to receive the centrifugate (dewatered microalgae paste) from the centrifuge along with an amount of fresh water in which the centrifugate may be resuspended. The resuspended biological material may be reintroduced into the centrifuge and mechanically processed. The centrate produced by this second centrifugation may contain an additional amount of entrained soluble chitosan, which may be communicated to the chitosan solution source 250.

Figure 2C:
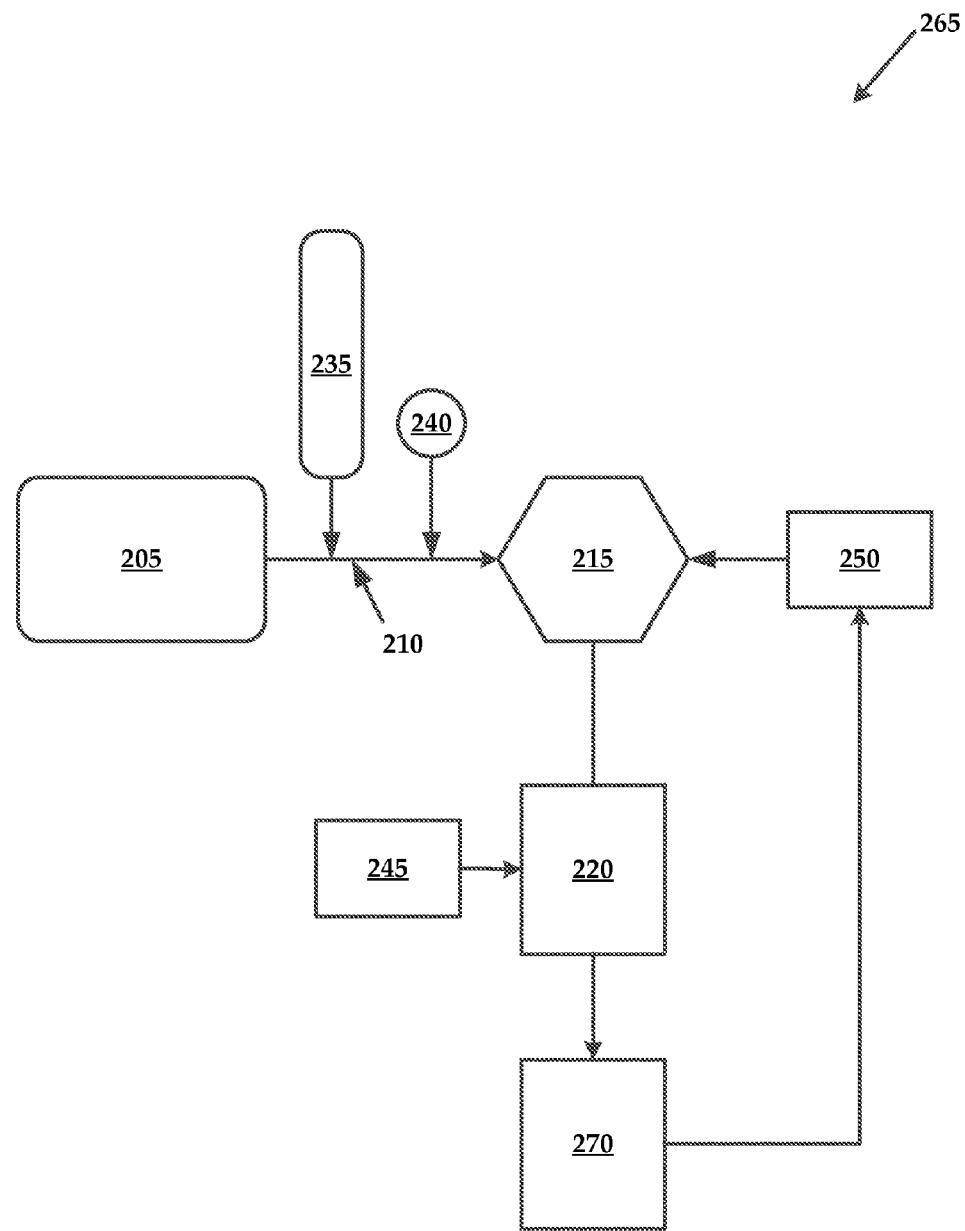
FIG. 2C illustrates a schematic diagram of an additional system adapted to utilize and recover chitosan for processing biological material in a continuous process.

Referring now to FIG. 2C, an additional embodiment of a system 265 adapted to utilize and recover chitosan for processing biological material is shown. The system 265 may be utilized to process microalgae in a continuous manner. It will be understood that the system 265 may include each of the components of system 200 (FIG. 2A) with the addition of an additional separator apparatus 270.

More specifically, rather than utilizing the separator apparatus 220 to both centrifuge the concentrated biological material and then centrifuge the resuspended biological material, the system 265 may include the additional separator apparatus 270 that is disposed downstream of the separator apparatus 220. The steps of resuspending the concentrated biological material and centrifuging the resuspended biological material occur in the additional separator apparatus 270, rather than in the separator apparatus 220. As such, the system 265 may continually process microalgae, as the system 265 does not require repeated use of the separator apparatus 220.

Figure 2D:
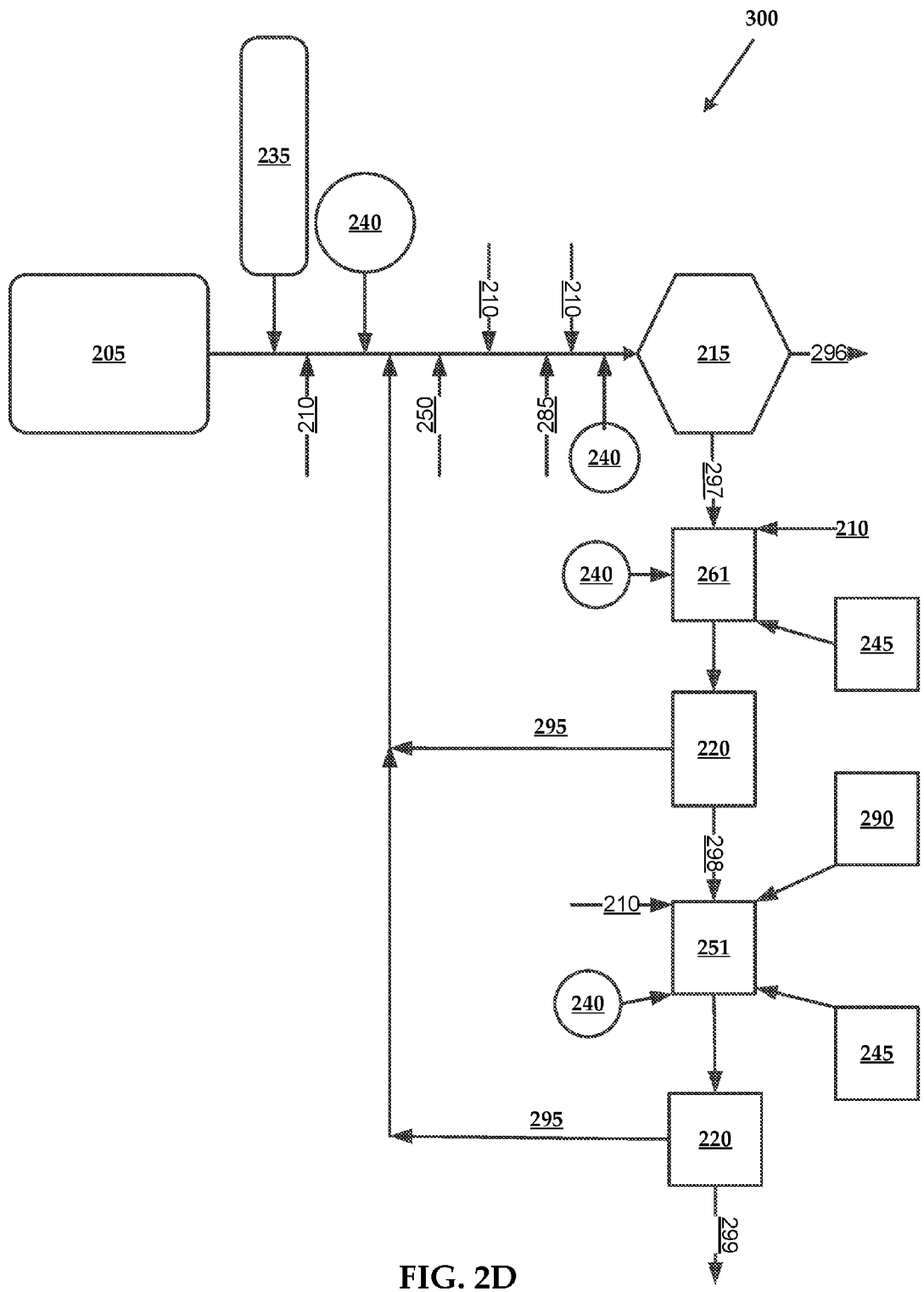
FIG. 2D illustrates a schematic diagram of an additional system adapted to utilize and recover chitosan for processing biological material in a continuous process.

Referring now to FIG. 2D, an additional embodiment of a system 300 adapted to utilize and recover chitosan for processing biological material is shown.

FIG. 2D shows culture source 205, mixer 210, flocculation apparatus 215, separator apparatus 220, pH probe 240, acid source 245, chitosan source 250, vessel 251, concentrate acidification 261, base source 285, fresh water source 290, centrate return of recycled chitosan 295, clarified media flow 296, concentrated flocculate flow 297, algae paste/concentrated biological material flow 298, and low ash algae paste/concentrated biological material flow 299.

According to some exemplary embodiments, culture source 205 is acidified (e.g., carbon dioxide or hydrochloric acid) via acid source 245. After mixing by mixer 210, the pH is measured by pH probe 240. In some embodiments, the pH should be approximately 5.8. Fresh chitosan solution is then added by chitosan source 250, and mixed by mixer 210. Base (e.g. sodium hydroxide or calcium hydroxide) is added by base source 285, and mixed by mixer 210. pH is then measured by pH probe 240. In some embodiments, the pH should be approximately 8.7. The mixture then flows into flocculation apparatus 215. Concentrated flocculates pass through concentrated flocculate flow 297 to the step of concentrate acidification 261, and for further mixing by mixer 210, acidification (e.g. hydrochloric acid) from acid source 245, and pH measurement by pH probe 240. In some embodiments, the pH should be approximately 3.5. The resulting mixture then flows into separator apparatus (e.g. centrifuge) 220. After separation, recycled chitosan is sent via centrate return of recycled chitosan 295 back into the system just prior to the chitosan source 250. Also, algae paste/concentrated biological material flows via algae paste/concentrated biological material flow 298 to vessel 251. At vessel 251, the algae paste/concentrated biological material receives fresh water from fresh water source 290, acid (e.g. hydrochloric acid) from acid source 245, and is mixed by mixer 210. A pH is measured by pH probe 240. In some embodiments, the pH should be approximately 3.5. Afterwards, the mixture is passed to separator (e.g. centrifuge) 220. After separation, the mixture is split between sending the low ash algae paste/concentrated biological material to low ash algae paste/concentrated biological material flow 299 and recycled chitosan via centrate return of recycled chitosan 295 back into the system just prior to the chitosan source 250.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

The invention claimed is:

1. A system adapted to utilize and recover chitosan for processing biological material, comprising:
   a culture source that retains culture, the culture including an amount of biological material suspended within a fluid;
   a mixer in fluid communication with the culture source and an acid source, the mixer adapted to reduce the pH of an amount of the culture to about 5 to 7, inclusive, by facilitating one or more chemical processes within the culture;
   a flocculation apparatus receiving the culture and incorporating an amount of a chitosan solution into the culture to form a mixture, wherein chitosan in the chitosan solution binds to the biological material, the flocculation apparatus adapted to then receive an amount of a base from a base source to increase the pH of the mixture to about 7 to 10, inclusive, to cause the biological material bound to the chitosan to form flocculates that are dispersed in the fluid and subsequently concentrated; and
   a separator apparatus to separate concentrated biological material from the concentrated flocculates, the separator apparatus being adapted to receive an amount of an acid to reduce the pH of the concentrated flocculates to about 3 to 5, inclusive, to remove recovered chitosan from the concentrated biological material;
   wherein the recovered chitosan and the concentrated biological material are mechanically processed by the separator apparatus to separate the recovered chitosan from the concentrated material; and
   wherein the recovered chitosan is incorporated with the chitosan solution.

2. The system according to claim 1, wherein the biological material includes microalgae cells of the genus *Nannochloropsis*.

3. The system according to claim 1, wherein the one or more chemical processes include at least one of:
   sparging an amount of carbon dioxide into the culture; and
   combining the amount of the culture with an amount of an acid.

4. The system according to claim 1, wherein the amount of chitosan solution incorporated includes about 0.5 to 200 milligrams of chitosan per liter of the culture.

5. The system according to claim 1, wherein the mixer includes at least one static mixer.

6. The system according to claim 1, wherein the base includes at least one of calcium oxide, calcium hydroxide, sodium hydroxide, magnesium hydroxide, and ammonium hydroxide.

7. The system according to claim 6, wherein the amount of the base includes a sufficient amount to raise the pH of the mixture a sufficient amount to cause substantially all of the suspended biological material to form flocculates.

8. The system according to claim 1, wherein the flocculation apparatus includes a dissolved air flotation device adapted to create micro-bubbles that associate with the flocculates and carry the flocculates to a surface of the fluid.

9. The system according to claim 1, wherein the separator apparatus includes at least one of a filter or series of filters, a decanter, centrifuge, and combinations thereof.

10. The system according to claim 1, wherein the mixer and the flocculation apparatus are combined and the separator apparatus includes a centrifuge.

11. The system according to claim 1, wherein the recovered chitosan solution is returned to a source of the chitosan solution.

12. The system according to claim 1, further comprising:
   an additional vessel adapted to receive the concentrated biological material from the separator and combine the concentrated biological material with fresh water such that additional chitosan is removed from the concentrated biological material;
   wherein the concentrated biological material combined with fresh water are provided to the separator to extract additional chitosan from the concentrated biological material.

13. The system according to claim 1, further comprising an additional separator apparatus adapted to receive the concentrated biological material from the separator and combine the concentrated biological material with fresh water, wherein the additional separator is adapted to mechanically process the concentrated biological material combined with fresh water to extract additional chitosan from the concentrated biological material.

14. The system according to claim 13, wherein mechanically process includes at least one of filtering, decanting, centrifuging, and combinations thereof.

* * * * *